(12) United States Patent
Sharpe et al.

(10) Patent No.: US 7,497,686 B2
(45) Date of Patent: Mar. 3, 2009

(54) BONE REGENERATION

(75) Inventors: Paul Thomas Sharpe, London (GB);
Michael David Leek, Cheshire (GB);
Paul David Kemp, Romiley (GB);
Ewan James Campbell, Cheshire (GB)

(73) Assignees: Odontis Ltd., London (GB); Intercytek Ltd., Manchester (GB)

( * ) Notice: Subject to any disclaimer, the term of this patent is extended or adjusted under 35 U.S.C. 154(b) by 352 days.

(21) Appl. No.: 11/171,965

(22) Filed: Jun. 30, 2005

(65) Prior Publication Data

US 2006/0057542 A1 Mar. 16, 2006

Related U.S. Application Data

(60) Provisional application No. 60/606,826, filed on Sep. 2, 2004.

(51) Int. Cl.
*A61C 5/00* (2006.01)

(52) U.S. Cl. ...................... 433/215; 623/17.17

(58) Field of Classification Search ............... 433/167, 433/172, 173, 202.1, 215, 219, 229; 424/93.21; 623/16.11, 17.17; 435/366
See application file for complete search history.

(56) References Cited

U.S. PATENT DOCUMENTS

| | | | | | |
|---|---|---|---|---|---|
| 3,514,858 | A | * | 6/1970 | Silverman | 433/174 |
| 4,725,234 | A | * | 2/1988 | Ethridge | 433/215 |
| 5,681,167 | A | * | 10/1997 | Lazarof | 433/174 |
| 5,695,338 | A | * | 12/1997 | Robert | 433/215 |
| 6,019,764 | A | * | 2/2000 | Bartee | 606/86 |
| 6,149,434 | A | * | 11/2000 | Gault | 433/215 |
| 6,402,518 | B1 | * | 6/2002 | Ashman | 433/215 |
| 6,409,764 | B1 | * | 6/2002 | White et al. | 623/16.11 |
| 6,413,089 | B1 | * | 7/2002 | Ashman et al. | 433/174 |
| 2002/0192198 | A1 | * | 12/2002 | Elia | 424/93.21 |
| 2003/0103950 | A1 | * | 6/2003 | Sharpe | 424/93.21 |
| 2004/0067467 | A1 | * | 4/2004 | Gault | 433/173 |
| 2004/0071637 | A1 | * | 4/2004 | Elia | 424/50 |
| 2004/0166100 | A1 | * | 8/2004 | Elia | 424/93.21 |
| 2007/0003529 | A1 | * | 1/2007 | Sharpe | 424/93.21 |

(Continued)

FOREIGN PATENT DOCUMENTS

EP 1 259 593 8/2001

(Continued)

OTHER PUBLICATIONS

Vincent Kokich, What's New in Dentistry, Angle Orthodontist, vol. 75, No. 1, 2005, pp. 144-145.*

(Continued)

*Primary Examiner*—John J Wilson
*Assistant Examiner*—Hao D Mai
(74) *Attorney, Agent, or Firm*—Fulbright & Jaworski LLP

(57) ABSTRACT

The present invention is based on the discovery that when a tooth primordium is inserted into a mammalian jaw and tooth formation follows, new alveolar bone around the new tooth forms. The present invention is based on the idea of stimulating new tooth formation via the implantation of tooth primordia at selected places in the jaw (e.g. at four points in the molar regions) to result in the formation of bony protuberances which could facilitate denture retention. The teeth may then be removed from the jaw of the patient to leave the new alveolar bone.

7 Claims, 4 Drawing Sheets

U.S. PATENT DOCUMENTS

2007/0071736 A1\* 3/2007 Elia .................. 424/93.21

FOREIGN PATENT DOCUMENTS

| WO | WO-00/30695 | 6/2000 |
| --- | --- | --- |
| WO | WO-01/60981 | 8/2001 |
| WO | WO-02/17983 | 3/2002 |
| WO | WO-02/40071 | 5/2002 |
| WO | WO-2004/074464 | 9/2004 |

OTHER PUBLICATIONS

Daily Mail, "Is this the end of dentures?" found online at http://www.dailymail.co.uk/pages/live/articles/health/thehealthnews.html?in_article_id=264317&in$_{13}$ page_id=1797, May 4, 2004.

Daily Mail, "Grow your own new teeth," found online at http://www.dailymail.co.uk/pages/live/articles/health/healthmain.html?in_article_id=310873&in_page_id=1774, Jul. 20, 2004.

Ferguson et al., "Activin is an essential early mesenchymal signal in tooth development that is required for patterning of the murine dentition," Genes & Development, 12: 2636-2649, 1998.

Ferguson et al., "Temporospatial cell interactions regulating mandibular and maxillary arch patterning," Development, 127: 403-412, 2000.

Grigoriou et al., "Expression and regulation of Lhx6 and Lxh7, a novel subfamily of LIM homeodomain encoding genes, suggests a role in mammalian head development," Development, 125:2063-2074, 1998.

Gronthos et al., "Postnatal human dental pulp stem cells (DPSCs) in vitro and in vivo," PNAS, 97(25): 13625-13630, 2000.

Hardcastle et al., "The Shh signaling pathway in tooth development: defects in Gli2 and Gli3 mutants," Development, 125:2803-2811, 1998.

Lumsden, "Spatial organization of the epithelium and the role of neural crest cells in the initiation of the mammalian tooth germ," Development, 103(Suppl.): 155-169, 1988.

MacKenzie et al., "Expression patterns of the homeobox gene, Hox-8, in the mouse embryo suggest a role in specifying tooth initiation and shape," Development, 115:403-420, 1992.

MacKenzie et al., "The homeobox gene Hox 7.1 has specific regional and temporal expression patterns using early murine craniofacial embryogenesis, especially tooth development in vivo and in vitro," Development, 111:269-285, 1991.

Ohazama et al., "Stem-cell-based Tissue Engineering of Murine Teeth," J. Dent. Res., 83(7): 518-522, 2004.

Satokata et al., "Msx1 deficient mice exhibit cleft palate and abnormalities of craniofacial and tooth development," Nature Genetics, 6:348-355, 1994.

Thomas et al., "Role of Dix-1 and Dix-2 genes in patterning of the murine dentition," Development, 124: 4811-4818, 1997.

Aberg et al, "Expression Patterns on Bone Morphogenetic Proteins (Bmps) in the Developing Mouse Tooth Suggest Roles in Morphogenesis and Cell Differentiation," Developmental Dynamics 210, 1997, pp. 383-396.

Acampora, D., et al., Craniofacial, vestibular and bone defects in mice lacking the Distal-less related gene Dlx5, Development (1999) 126, 3795-3809.

Asashime et al, "Mesodermal induction in early amphibian embryos by activin A (erthroid differentiation factor)" Roux's Archives of Developmental Biology 198; 1990, pp. 330-335.

Baba et al., "Determination of enamel protein synthesized by recombined mouse molar tooth germs in organ culture", Archives of Oral Biology, Feb. 1996, 215-219(5), vol. 41(2).

Bagutti et al, "Differentiation of Embryonal Stem Cells into Keratinocytes: Comparison of Wild-Type and B1 Intergrin-Deficient Cells," Developmental Biology 179, 1996, pp. 184-196.

Bitgood et al, "Hedgehog anf Bmp Genes Are Coexpressed at Many Diverse Sites of Cell-Cell Interaction in the Mouse Embryo," developmental Biology 172, 1995, pp. 126-138.

Chai et al, "Specific Transforming Growth Factor-B Subtypes Regulate Embryonic Mouse Meckel's Cartilage and tooth Development," Developmental Biology 162, 1994, pp. 85-103.

Chen et al, "Msx1 Controls Inductive Signaling in Mammalian Tooth Morphogenesis," Developmental 122, 1996, pp. 3035-3044.

Cobourne et al., "Sonic hedgehog Regulates Epithelial Proliferation and Cell Survival in the Developing Tooth Germ," J. Dent. Res., 80(11): 1974-1979, 2001.

Conlon et al, "A Primary Requirement for Nodal in the Formation and Maintenance of the Primitive Streak in the Mouse," Development 120, 1994, pp. 1919-1928.

Crossley et al, "The Mouse Fgf8 Gene Encodes a Family of Polypeptides and is Expressed in Regions that Direct Outgrowth and Patterning in the Developing Embryo," Developmental 121, 1995, pp. 439-451.

De Winter et al, "Follistatins Neutralized Activin Bioactivity by Inhibition of Activin Binding to its type II Receptors," Molecular and Cellular Endocrinology 116, 1996, pp. 105-114.

Dohrmann et al, "Expression of Activin mRNA during Early Development in Xenopus laevis," Developmental Biology 157, 1993, pp. 474-483.

Dyson et al, "Activin Signaling has a Necessary Function in Xenopus Early development," Current Biology 7, 1997, pp. 81-84.

Fainsod et al, "The Dorsalizing and Neural Inducing Gene Follistatin is an Antagonist of BMP-4," Mechanism of Development 63, 1997, pp. 39-50.

Feijen et al, "Expression of activin Subunits, Activin Receptors and Follistatin in Postimplantation Mouse Embryos Suggests Specific developmental Functions for Different activins," Development 120, 1994, pp. 3621-3637.

Ferguson et al., "The role of effectors of the activin signalling pathway, activin receptors IIA and IIB, and Smad2, in patterning of tooth development," Development, 128: 4605-4613, 2001.

Fong et al., "The crowning achievement: getting to the root of the problem", J Dent Educ., May 2005, 555-70, vol. 69(5).

Gage et al, "Dosage Requirement of Pitx2 for Development of Multiple Organs," Development 126, 1999, pp. 4643-4651.

Green et al, "Graded Changes in Dose of a Xenopus Activin A Homologue Elicit Stepwise Transitions in Embryonic Cell Fate," Nature vol. 347, Sep. 1990, pp. 391-394.

Green et al, "Responses of Embryonic Xenopus Cells to Activin and FGF are seperated by Multple Dose Thresholds and Correspond to Distinct Axes of the Mesoderm," Cell vol. 71, Nov. 27, 1992, pp. 731-739.

Green et al., "Antagonistic Regulation of Dlx2 Expression by PITX2 and Msx2: Implications for Tooth Development," Gene Expression, 9: 265-281, 2001.

Heikinheimo et al, "Fgf-8 Expression in the Post-Gastrulation Mouse Suggests roles in the Development of the Face, Limbs and Central Nerous System," Mechanisms of Development 48 48, 1994, pp. 129-138.

Heikinheimo et al, "The Activin-binding Protein Follistatin is Expressed in Developing Murine Molar and Induces Odontoblast-like Cell Differentiation in vitro," J. Dent Res 76 (10), Oct. 1997, pp. 1625-1636.

Heiko Peters, Annette Neubüser, Klaus Kratochwil and Rudi Balling, Pax9-deficient mice lack pharyngeal pouch derivatives and teeth and exhibit craniofacial and limb abnormalities, Genes & Dev. (1998) 12: 2735-2747.

Hemmati-Brivanlou et al, "A Truncated Activin Receptor Inhibits Mesoderm Induction and Formation of Axial Structures in Xenopus Embryos," Nature vol. 359, Oct. 15, 1992, pp. 609-614.

Hemmati-Brivanlou et al, "Follistatin, an Antagonist of Activin, is expressed in the Spemann Organizer and Dsiplays Direct Neuralizing Activity," Cell Feb. 24, 1994, 283-295.

Hemmati-Brivanlou et al, "Inhibition of Activin Receptor Signaling Promotes Neuralization in Xenopus," Cell, Feb. 24, 1994, pp. 273-281.

Iseki et al, "Sonic Hedgehog is Expressed in Epithelial Cells During Development of Whisker, Hair and Tooth," Biochemical and Biophysical Research Communications 218, 1996, pp. 688-693.

Kettunen et al, "Expression and Function of FGFs -4, -8, and -9 Suggest Functional Redundancy and Repetitive Use as Epithelial Signals During Tooth Morphogenesis," developmental Dynamics 211, 1998, pp. 256-268.

Kettunen et al., "Associations of FGF-3 and FGF-10 in signaling networks regulating tooth morphogenesis", Dev. Dyn., 2000, 322-332, vol. 219.

Kollar et al., "The Influence of the Dental Papilla on the Development of Tooth Shape in Embryonic Mouse Tooth Germs," J. Embryol. Exp. Morph. vol. 21, Feb. 1969, pp. 131-148.

Kratochwil et al, "Lef1 Expression is Activated by BMP-4 and Regulates Inductive Tissue Interactions in Tooth and Hair Development," Gene & Development 10, 1996, pp. 1382-1394.

Lin et al, "Pitx2 Regulates Lung Asymmetry, Cardiac Positioning and Pituitary and Tooth Morphogenesis," Nature vol. 401, Sep. 16, 1999, pp. 279-282.

Linden GJ. Bone induction in implants of decalcified bone and dentine. J Anat. Apr. 1975;119(Pt 2):359-67.

Long et al., "Osteogenesis and Bone-Marrow-Derived Cells", Blood Cells, Molecules, and Diseases, May 2001, 677-690, vol. 27(3).

Lu et al, "Function of Rieger Syndrome Gene in Left-Right Asymmetry and Craniofacial Development," Nature vol. 401, Sep. 16, 1999, pp. 276-278.

Masella et al., "Current concepts in the biology of orthodontic tooth movement", Am J Orthod Dentofacial Orthop, 2006, 458-468, vol. 129.

Matzuk et al, "Different Phenotypes for Mice Deficient in Either Activins or Activin Receptor Type II," Nature vol. 374, Mar. 23, 1995, pp. 356-360.

Matzuk et al, "Functional Analysis of Activins During Mammalian Development," Nature vol. 374, Mar. 23, 1995, pp. 354-356.

Matzuk et al, "Multiple Defects and Perinatal Death in Mice Deficient in Follistatin," Nature Nol. 374, Mar. 23, 1995, pp. 360-363.

Michel et al, "Follistatins: More than Follicle-Stimulating Hormone Supressing Proteins," Molecular and Cellular Endocrinology 91, 1993, pp. 1-11.

Mina et al, "The induction of Odontogenesis in Non-Dental Mesenchyme Combined with Early Murine Mandibular Arch Epithelium," Archs Oral Biol., vol. 32, No. 2, 1987, pp. 123-127.

Miura et al., "SHED: Stem cell form human exfoliated deciduous teeth," *PNAS*, 100(10): 5807-5812, 2003.

Morio I. Recombinant study of the mouse molar cervical loop and dental papilla by renal transplantation. Arch Oral Biol. 1985;30(7):557-61. (PUBMED ABSTRACT).

Mucchielli et al, "Mouse Otlx2/RIEG Expression in the Odontogenic Epithelium Precedes Tooth Initiation and Requires Mesenchyme-Derived Signals for Its Maintenance," Developmental Biology 189, 1997, pp. 275-284.

Nakamura et al., "Activin-Binding Protein from Rat Ovary is Follistatin," Science vol. 247, Feb. 1990, pp. 836-838.

Neubuser et al, "Antagonistic Interactions between FGF and BMP Signaling Pathways: A Mechanism for Positioning the Sites of Tooth Formation," Cell vol. 90, Jul. 25, 1997, pp. 247-255.

Ohkubo et al., "Coordinate regulation and synergistic actions of BMP4, SHH and FGF8 in the rostral prosencephalon regulate morphogenesis of the telencephalic and optic vesicles", Neuroscience, Apr. 22, 2002, 1-17, vol. 111(1).

Pownall et al, "eFgF, Xcad3 and Hox genes form a molecular Pathway that Establishes the Anteroposterior Axis in *Xenopus*," Development 122, 1996, pp. 3881-3892.

Qiu et al, "Role of the Dlx Hoeobox Genes in Proximodistal Patterning of the Branchial Arches: Mutations of Dlx-1, Dlx-2 and Dlx-1 and -2 Alter Morphogenesis of Proximal Skeletal and Soft Tissue Structures Derived from the First and Second Arches," Developmental Biology 185, 1997, pp. 165-184.

Quint et al., "Differential expression of orthologous Dlx genes in zebrafish and mice: Implications for the evolution of the Dlx homeobox gene family", Journal of Experimental Zoology, Molecular and Developmental Evolution, 2000, 235-241, vol. 288(3).

Rathjen et al, "Formation of a Primitive Ectoderm like Cell Population, EPL cells, from ES Cells in response to Biologically Derived Factors," Journal of Cell Science 112, 1999, pp. 601-612.

Ringe et al., "Stem cell for regenerative medicine: advances in the engineering of tissues and organs," *Naturwissenschaften*, 89: 338-351, 2002.

Roberts et al, "Expression of Inhibin/Activin Subunit Messenger Ribonucleic Acids during Rat Embryogenesis," Endocrinology vol. 128, No. 6, 1991, pp. 3122-3129.

Roberts et al, "Expression of Messenger Ribonucleic Acids Encoding the Inhibin/Activin System during Mid-and Late-Gestation Rat Embryogenesis," Endocrinology vol. 134, No. 2, 1994, pp. 914-923.

Sarkar et al, "Inhibition of Wnt Signaling by Exogenous Mfrzb1 Protein Affects Molar Tooth Size," Journal of Dental research vol. 79, No. 4, 2000, pp. 920-925.

Saxen, Lauri. "Effect of Tetracycline on Osteogenesis in Vitro," J. Exp. Zool. 162; pp. 269-294.

Semina et al, "Cloning and Characterization of a Novel Bicoid-related Homeobox Transcription Factor Gene, RIEG, involved in Reiger Syndrome," Nature Genetics vol. 14, Dec. 1996, pp. 392-399.

Sharpe et al., "Test-Tube Teeth", Scientific American Magazine, Aug. 2005, 34-41, vol. 293(2).

Sporn et al., "Peptide Growth Factors and their Receptors II", Springer, Berlin 1990, 179-210.

Teixeira, Cristina, "New Horizons in Understanding Early Tooth development," Clin. Orthod. Res. 2, 1999, pp. 171-174.

Thesleff et al, "Molecular Regulation of Tooth Development," Bone vol. 25, No. 1, Jul. 1999, pp. 123-125.

Thesleff et al, "Regulation of Organogenesis. Common Molecular Mechanisms Regulating the Development of Teeth and Other Organs," Int. J. Dev. Biol. 39, 1995, pp. 35-50.

Thesleff et al, "Signalling Networks Regulating Dental Development," Mechanisms of Development 67, 1997, pp. 111-123.

Thesleff et al., "The Role of Growth Factors in Tooth Development," *International Review of Cytology*, 217: 93-135, 2002.

Thesleff, "Developmental biology and building a tooth," *Dental Research*, 34(8): 613-620, 2003.

Thesleff, Irma, "Genetic Basis of Tooth Development and Dental Defects," Acta Odontol Scand 58, 2000, pp. 191-194.

Thomas et al, "The Spatial Localization of Dlx-2 During Tooth Development," Connective Tissue Research vol. 32, No. 1-4, 1995, pp. 27-34.

Thomas et al., "Differentiation of odontoblasts in grafted recombinants of murine epithelial root sheath and dental mesenchyme", Arch Oral Biol, 1989, 27-35, vol. 34(1).

Thomsen et al, "Activins are Expressed Early in *Xenopus* Embryogenesis an Can Include Axial Mesoderm and Anterior Structures," Cell vol. 63, Nov. 2, 1990, pp. 485-493.

Tissier-Seta et al, "Barx1, a New Mouse Homeodomain Transcription Factor Expressed in cranio-Facial Ectomesenchyme and the Stomach," Mechanisms of Development 51, 1995, pp. 3-15.

Trowell, O.A., "The Culture of Mature Organs in a Synthetic Medium," Experimental Cell Research 16, p. 118-147, 1959.

Tucker et al, "Transformation of Tooth Type Induced by Inhibition of BMP Signaling," Science vol. 282, Nov. 6, 1998, pp. 1136-1138.

U.S. Appl. No. 10/204,208, Filing or 371 (c) Date: Oct. 30, 2002, Title: "Tooth Progenitor Cell and Method for Its Production", File History, Requirement for Restriction/Election, Sep. 19, 2005.

U.S. Appl. No. 10/204,208, Filing or 371 (c) Date: Oct. 30, 2002, Title: "Tooth Progenitor Cell and Method for Its Production", File History, Applicant Arguments/Remarks Made in an Amendment, Nov. 16, 2005.

U.S. Appl. No. 10/204,208, Filing or 371 (c) Date: Oct. 30, 2002, Title: "Tooth Progenitor Cell and Method for Its Production", File History, Claims, Nov. 16, 2005.

U.S. Appl. No. 10/204,208, Filing or 371 (c) Date: Oct. 30, 2002, Title: "Tooth Progenitor Cell and Method for Its Production", File History, Response to Election / Restriction Filed, Nov. 16, 2005.

U.S. Appl. No. 10/204,208, Filing or 371 (c) Date: Oct. 30, 2002, Title: "Tooth Progenitor Cell and Method for Its Production", File History, Non-Final Rejection, Feb. 13, 2006.

U.S. Appl. No. 10/204,208, Filing or 371 (c) Date: Oct. 30, 2002, Title: "Tooth Progenitor Cell and Method for Its Production", File History, Rule 130, 131 or 132 Affidavits, Jun. 13, 2006.

U.S. Appl. No. 10/204,208, Filing or 371 (c) Date: Oct. 30, 2002, Title: "Tooth Progenitor Cell and Method for Its Production", File History, Applicant Arguments/Remarks Made in an Amendment, Jun. 13, 2006.

U.S. Appl. No. 10/204,208, Filing or 371 (c) Date: Oct. 30, 2002, Title: "Tooth Progenitor Cell and Method for Its Production", File History, Claims, Jun. 13, 2006.

U.S. Appl. No. 10/204,208, Filing or 371 (c) Date: Oct. 30, 2002, Title: "Tooth Progenitor Cell and Method for Its Production", File History, Amendment—After Non-Final Rejection, Jun. 13, 2006.

U.S. Appl. No. 10/204,208, Filing or 371 (c) Date: Oct. 30, 2002, Title: "Tooth Progenitor Cell and Method for Its Production", File History, Final Rejection, Aug. 23, 2006.

U.S. Appl. No. 10/204,208, Filing or 371 (c) Date: Oct. 30, 2002, Title: "Tooth Progenitor Cell and Method for Its Production", File History, Applicant Arguments/Remarks Made in an Amendment, Jan. 23, 2007.

U.S. Appl. No. 10/204,208, Filing or 371 (c) Date: Oct. 30, 2002, Title: "Tooth Progenitor Cell and Method for Its Production", File History, Claims, Jan. 23, 2007.

U.S. Appl. No. 10/204,208, Filing or 371 (c) Date: Oct. 30, 2002, Title: "Tooth Progenitor Cell and Method for Its Production", File History, Amendment Submitted/Entered with Filing of CPA/RCE, Jan. 23, 2007.

U.S. Appl. No. 10/204,208, Filing or 371 (c) Date: Oct. 30, 2002, Title: "Tooth Progenitor Cell and Method for Its Production", File History, Rule 130, 131 or 132 Affidavits, Jan. 23, 2007.

U.S. Appl. No. 10/204,208, Filing or 371 (c) Date: Oct. 30, 2002, Title: "Tooth Progenitor Cell and Method for Its Production", File History, Request for Continued Examination (RCE), Jan. 23, 2007.

U.S. Appl. No. 10/204,208, Filing or 371 (c) Date: Oct. 30, 2002, Title: "Tooth Progenitor Cell and Method for Its Production", File History, List of references cited by examiner, Feb. 27, 2007.

U.S. Appl. No. 10/204,208, Filing or 371 (c) Date: Oct. 30, 2002, Title: "Tooth Progenitor Cell and Method for Its Production", File History, Non-Final Rejection, Feb. 27, 2007.

U.S. Appl. No. 10/204,208, Filing or 371 (c) Date: Oct. 20, 2002, Title: "Tooth Progenitor Cell and Method for Its Production", File History, Examiner Interview Summary Record (PTOL—413), May 16, 2007.

U.S. Appl. No. 10/204,208, Filing or 371 (c) Date: Oct. 30, 2002, Title: "Tooth Progenitor Cell and Method for Its Production", File History, Rule 130, 131 or 132 Affidavits, Aug. 27, 2007.

U.S. Appl. No. 10/204,208, Filing or 371 (c) Date: Oct. 30, 2002, Title: "Tooth Progenitor Cell and Method for Its Production", File History, Applicant Arguments/Remarks Made in an Amendment, Aug. 27, 2007.

U.S. Appl. No. 10/204,208, Filing or 371 (c) Date: Oct. 30, 2002, Title: "Tooth Progenitor Cell and Method for Its Production", File History, Supplemental Response or Supplemental Amendment, Aug. 27, 2007.

U.S. Appl. No. 10/204,208, Filing or 371 (c) Date: Oct. 30, 2002, Title: "Tooth Progenitor Cell and Method for Its Production", File History, Rule 130, 131 or 132 Affidavits , Aug. 27, 2007.

U.S. Appl. No. 10/204,208, Filing or 371 (c) Date: Oct. 30, 2002, Title: "Tooth Progenitor Cell and Method for Its Production", File History, Applicant Arguments/Remarks Made in an Amendment, Aug. 27, 2007.

U.S. Appl. No. 10/204,208, Filing or 371 (c) Date: Oct. 30, 2002, Title: "Tooth Progenitor Cell and Method for Its Production", File History, Claims, Aug. 27, 2007.

U.S. Appl. No. 10/204,208, Filing or 371 (c) Date: Oct. 30, 2002, Title: "Tooth Progenitor Cell and Method for Its Production", File History, Applicant summary of interview with examiner, Aug. 27, 2007.

U.S. Appl. No. 10/204,208, Filing or 371 (c) Date: Oct. 30, 2002, Title: "Tooth Progenitor Cell and Method for Its Production", File History, Amendment—After Non-Final Rejection, Aug. 27, 2007.

U.S. Appl. No. 10/204,208, Filing or 371 (c) Date: Oct. 30, 2002, Title: "Tooth Progenitor Cell and Method for Its Production", File History, Rule 130, 131 or 132 Affidavits, Oct. 9, 2007.

U.S. Appl. No. 10/204,208, Filing or 371 (c) Date: Oct. 30, 2002, Title: "Tooth Progenitor Cell and Method for Its Production", File History, Rule 130, 131 or 132 Affidavits , Oct. 9, 2007

U.S. Appl. No. 10/204,208, Filing or 371 (c) Date: Oct. 30, 2002, Title: "Tooth Progenitor Cell and Method for Its Production", File History, Applicant Arguments/Remarks Made in an Amendment, Oct. 9, 2007.

U.S. Appl. No. 10/204,208, Filing or 371 (c) Date: Oct. 30, 2002, Title: "Tooth Progenitor Cell and Method for Its Production", File History, Supplemental Response or Supplemental Amendment, Oct. 9, 2007.

U.S. Appl. No. 10/204,208, Filing or 371 (c) Date: Oct. 30, 2002, Title: "Tooth Progenitor Cell and Method for Its Production", File History, Final Rejection, Jan. 2, 2008.

Vaahtokari et al, "Associations between transforming Growth Factor B1 RNA Expression and Epithelial—mesenchymal Interactions During Tooth Morphogenesis," Development 113, 1991, pp. 985-994.

Vaahtokari et al, "The Enamel Knot as a Signaling Center in the Developing Mouse Tooth," Mechanisms of Development 54, 1996, pp. 39-43.

Vainio et al, "Identification of BMP-4 as a Signal Mediating Secdondary Induction between Epithelial and Mesenchymal Tissues during Early Tooth Develpoment," Cell vol. 75, Oct. 8, 1993, pp. 45-58.

Vale et al, "The Inhibin/Activin Family Hormones and Growth Factors," Peptide Growth Factors and Their Receptors II Chapter 26, Springer Verlag Berlin, Germany, 1990.

Van Genderen et al, "Development of Several Organs that Require Inductive Epithelial-mesenchymal Interactions is Impaired in LEF-1-deficient Mice," Genes & Development 8, 1994, pp. 2691-2703.

Verfaillie et al., "Stem Cells: Hype and Reality", Hematology, 2002, 369-91.

Wilkinson, David, "Whole Mount in Situ Hybridization of Vertebrate Embryos," In situ Hybridization, A Practical Approach Chapter 6, IRL Press, Oxford, UK, 1995.

Yamashita et al, "Osteogenic Protein-1 Binds to Activin Type II Receptors and induces Certain Activin-like Effects," The Journal of Cell biology, vol. 130, 1995, pp. 217-226.

* cited by examiner

A

D

BONE REGENERATION

CROSS-REFERENCE TO RELATED APPLICATIONS

This application claims priority to U.S. Provisional Application No. 60/606,826 filed Sep. 2, 2004, which is incorporated herein by reference in its entirety.

TECHNICAL FIELD

The present invention relates to the production of alveolar bone and to jaw augmentation.

BACKGROUND OF THE INVENTION

Many people experience tooth loss and require dentures. Unfortunately, many patients experience great difficulty in retaining dentures in position because the loss of teeth is accompanied with the subsequent loss of the alveolar bone (the tooth supporting bony ridge). The lack of any ridge on which to locate the denture plates then creates problems in retaining the dentures. Current bone graft procedures involve surgical insertion of either bone substitutes or grafts from rib or hip. These are significant surgical procedures which are not appropriate to the vast majority of edentulous (usually elderly) patients.

The present invention provides methods and compositions for facilitating denture retention which do not require significant surgery.

BRIEF SUMMARY OF THE INVENTION

The present invention relates to jaw augmentation and in particular to jaw augmentation for the purposes of facilitating denture retention. It has been found that when a tooth primordium is inserted into a mammalian jaw and tooth formation follows, new alveolar bone around the new tooth forms. The present invention is based on the idea of stimulating new tooth formation via the implantation of tooth primordia at selected places in the jaw (e.g. at four points in the molar regions) to result in the formation of bony protuberances which could facilitate denture retention. The teeth may then be removed from the jaw of the patient to leave the new alveolar bone.

The present invention has the advantage that the bony ("volcano-like") protuberances formed around the tooth are far easier to produce and more suitable for anchorage of dentures than bone formed by current methods of surgical implantation which require invasive surgical shaping.

Additionally, the present invention has the advantage that the formation of new alveolar bone is easier to achieve than tooth replacement as the management of shape, size, and orientation of the new tooth is not important.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

(FIGS. 1A, 1D) Lightfield photomicrograph showing epithelial bud formation in recombinant explants. (FIGS. 1B, 1C) Sections adjacent to (A) showing radioactive in situ hybridisation for Lhx7 (FIG. 1B) and Msx1 (FIG. 1C). (FIG. 1E) Section adjacent to (FIG. 1D) showing radioactive in situ hybridisation for Pax9 (FIG. 1E). Tooth germ epithelium is outlined. Scale bar: 100 µm.

(FIG. 2A) Lightfield photomicrograph showing localisation of epithelium in a recombinant explant. (FIGS. 2B-D) Sections adjacent to (FIG. 2A) showing radioactive in situ hybridisation for Lhx7 (FIG. 2B), Msx1 (FIG. 2C) and Pax9 (FIG. 2D). (FIGS. 2E-H) Adjacent sections of a recombination between bone marrow-derived cells and embryonic oral epithelium. (FIGS. 2E) Example of GFP expression in embryonic oral epithelium in a recombination. (FIGS. 2F-H) Expression of Lhx7 (FIG. 2F), Msx1 (FIG. 2G) and Pax9 (FIG. 2H) in bone marrow-derived cells adjacent to the embryonic oral epithelium. (FIG. 2I) Lightfield photomicrograph showing localisation of epithelium in recombinant explants. (FIG. 2J-L) Sections adjacent to (FIG. 2I) showing no expression of Lhx7 (FIG. 2J), Msx1 (FIG. 2K) and Pax9 (FIG. 2L). Tooth germ epithelium is outlined. Scale bar: 100 µm.

FIG. 3A shows incisors. FIG. 3B shows first molar. FIG. 3C shows second molar. FIG. 3D shows third molar. FIG. 3E shows ectopic tooth in diastema region (between FIGS. 3A and 3B). Arrows show ectopic bone. FIG. 3F shows high magnification of boxed area in FIG. 3E, showing periodontal ligament-like tissue. d=dentin. pd=pre-dentin. Scale bars: 1.2 mm (FIGS. 3A-D); 1.0 mm (FIG. 3E); 50 µm (FIG. 3F).

DETAILED DESCRIPTION OF THE INVENTION

Figure 1:
FIGS. 1A-1E show sections of heterotypic recombinations between ES cell aggregations and embryonic oral epithelium.
Figure 1:
Figure 1:
Figure 1:
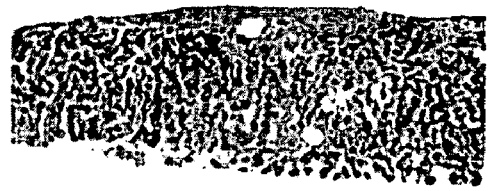
Figure 1:
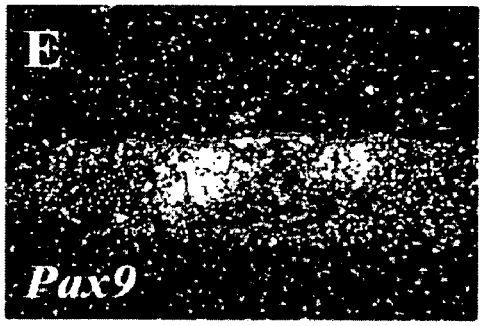

A first aspect of the invention provides a method of jaw augmentation, the method comprising implanting a tooth primordium into a space in the oral cavity of the patient and allowing the tooth primordium to develop into a tooth.

Preferably, the jaw augmentation is for the purpose of creating one or more bony protuberances which can facilitate denture retention. Alternatively, the jaw augmentation may be for the purpose of tooth replacement or for the treatment of periodontal disease.

Accordingly, in a preferred embodiment of the first aspect of the invention, there is provided a method of regenerating alveolar bone for facilitating denture retention, the method comprising: i) implanting a tooth primordium into a space in the oral cavity of the patient and allowing the tooth primordium to develop into a tooth; and ii) removing the tooth to thereby leave a bony protuberance in the patient's jaw to facilitate denture retention.

Preferably, the method comprises the following further step: iii) creating a denture for the patient which denture is to be held in place at least partly by the bony protuberance.

Preferably, the tooth primordium used in step i) of the invention is created by inducing stem cells from the patient (e.g. neural stem cells, embryonic stem cells, bone marrow cell stem cells or stem cells from the patients remaining teeth/teeth cells (which may for example be found in dental pulp and from exfoliated deciduous teeth) to undergo odontogenesis to form tooth progenitor cells and tooth primordia.

A second aspect of the invention provides the use of stem cells in the manufacture of a medicament for jaw augmentation.

A third aspect of the invention provides the use of a tooth primordium in the manufacture of a medicament for jaw augmentation.

In the second and third aspects of the invention, it is preferred that the jaw augmentation is carried out for the purpose of creating bony protuberances which facilitate denture retention.

Preferably, the tooth primordia used in the methods and uses of the present invention are produced from cells from the patient being treated. This avoids the problem of graft rejection. Thus, in a preferred embodiment the tooth primordia used are produced using stem cells from the patient undergoing treatment.

A fourth aspect of the invention provides a method of making a denture which is to retained by the patient at least partly by one or more bony protuberances created by the method of the first aspect of the invention, the method comprising making a model (e.g. an impression) of at least part of a patient's jaw which patient has undergone jaw augmentation according to the method of the first aspect of the invention and using the model to create the denture.

A fifth aspect of the invention provides a denture made by the process of the fourth aspect of the invention.

Preferably, the patient is a human patient. Preferably, the patient is an adult (greater than 18 years of age) and more preferably the patient is middle-aged (e.g. greater than 45 years of age) or is an elderly patient (e.g. greater than 65 years of age).

Tooth Primordia Production

Tooth development requires the combination of cells from mesenchymal and epithelial lineages. Development of the mammalian tooth has been recognised as a model system for study of epithelial/mesenchymal interactions during organogenesis. Teeth start to develop early in mammalian embryogenesis (11 days in mice, 6 weeks in humans), from a series of reciprocal interactions between two cell types: oral epithelial cells and neural crest-derived mesenchyme cells.

Inductive signals for tooth development come from the epithelium whereupon the responding mesenchymal cells are programmed to become odontogenic (Lumsden, 1988).

Odontogenic mesenchymal cells then provide instructive signals for further tooth development (Thesleff and Sharpe, 1997). The epithelial cells eventually give rise to ameloblasts which are responsible for enamel formation and mesenchyme cells form odontoblasts which produce dentine and cementoblasts.

The identity of these different instructive signals has been revealed by gene expression studies and implantation experiments. FGF8, BMP4 and SHH are established as early instructive signals from the oral epithelium (Thesleff and Sharpe, 1997). BMP's, FGF's and activin are among the early signals from the mesenchyme (Thesleff and Sharpe, 1997; Ferguson et al., 1998).

Prior art approaches to the production of tooth primordia have included in vitro tissue recombination. In this approach, two different tissue types are independently dissected from the animal embryo, and these tissues are recombined in the laboratory. Signals from one may then induce formation of tooth primordia in the other. This is a labour intensive process carried out by highly trained workers involving a great deal of surgical skill.

In an alternative approach, Young et al. has showed that cells dissociated from early tooth buds when cultured on a matrix and implanted into an adult animal can form teeth, indicating the presence of both epithelial and mesenchymal dental stem cells (Young et al., 2002).

For human therapeutic purposes the major drawback is the potential problem of graft rejection, thus requiring either immunosuppression of host (recipient), or genetic manipulation of the graft cells to circumvent rejection, and the difficulty of obtaining the cells. Therefore the use of cells derived exclusively from each patient would avoid such rejection problems.

Sharpe (WO 01/60981) showed that cultured embryonic stem cells can give rise to epithelial and mesenchyme lineages, enabling the production of teeth primordia from embryonic stem cells. However, the use of embryonic stem cells requires purification and expansion of a population of cells. This involves intricate and highly skilled separation and manipulation techniques. Another problem associated with the use of embryonic stem cells is the limited availability and ease with which the embryonic stem cells can be obtained.

Adult (i.e. non-embryonic) bone marrow cells are known to contain populations of stem cells and pluripotential cells which give rise to (a) haematopoietic cells and (b) stromal (mesenchymal) cells. Haematopoietic cells in the bone marrow, however, do not give rise to non-haematopoietic tissues (Wagers et al). Mesenchymal stem cells give rise to homogeneous differentiated cell types of tissues including bone, cartilage, fat, muscle, tendon, hematopoiesis-supporting stroma, and mesangial tissues, but are not known to be capable of forming organs of composite cell lineages and those that require specific reciprocal tissue interactions, such as teeth whose development requires contributions from more than one cell lineage.

PCT/GB2004/000635 documents the surprising discovery that bone marrow cells may be employed to produce tooth primordia. The use of bone marrow cells obviates the need for purification and expansion of a population of cells. Since bone marrow cells may be obtained from any individual, the use of such cells in therapeutic tooth formation offers (a)

avoidance of problems of graft rejection, and (b) wider accessibility of the pluripotent cell component compared with embryonic stem cells. In a preferred embodiment of the invention, bone marrow cells are used in the production of the tooth primordia.

In one embodiment, the bone marrow cells have not undergone purification for a particular cell type. By "purification for a particular cell type" we refer to any process which increases the proportion of a particular type of bone marrow cell present by removal of one or more other cell types present in the unpurified cell population.

Preferably, the unpurified bone marrow cells have not undergone expansion to increase the proportion of a particular cell type present. Alternatively, the unpurified bone marrow cells have undergone expansion to increase the proportion of a particular cell type present.

In another embodiment, the bone marrow cells have undergone purification for a particular cell type, for example to increase the proportion of bone marrow stem cells present. Techniques for obtaining a purified cell population will be well known to those skilled in the art.

Preferably, the purified bone marrow cells have undergone expansion (either before or after purification; preferably after purification). In this way increased numbers of a particular cell type present may be obtained.

Tooth progenitor cells may be produced by incubating bone marrow cells in the presence of oral epithelial inductive signals. Suitably, at least about 100, 500, 1000, 2500, 5000, 7500, 10000 or 15000 bone marrow cells are incubated in the presence of oral epithelial inductive signals.

The bone marrow cells are preferably obtained from a single individual. Alternatively, the bone marrow cells may be obtained from a number of individuals and pooled.

The bone marrow cells may be prepared for the induction/interaction in a number of ways. For example, they may be pelleted to form small aggregates. This may be accomplished by pelleting them onto filters. Such filters may comprise any suitable substrate, such as pregelatinized Millipore filters. For convenience, the filters may be supported by metal grids, for example as described in Ferguson et al. (1998). The bone marrow cells may be pelleted into small holes made in a gel or other suitable semi-solid support. The gel may be a collagen gel. The gel may be Collaborative Biomedical Products' Matrigel or a similar substrate.

Optionally, epithelium may be overlaid onto the bone marrow cells to cover the hole which is then covered with a thin layer of gel and incubated.

Gels used in this manner may themselves be supported by membrane(s) and/or metal grids.

The bone marrow cells are contacted with oral epithelial inductive signals. Preferably, the bone marrow cells are contacted with any combination of one, two, three or all of the following: FGF8, BMP4, SHH and WNTS. As discussed below, the oral epithelial inductive signals may be provided by a variety of means some of which do not require the presence of embryonic oral epithelial cells.

Examples of epithelial markers include Pitx2, p21, Wnt7b and others. These markers may be detected by any suitable means, such as western blotting, immunofluorescence, radioactive in situ hybridization or other suitable means.

Genes known to be expressed in tooth germ epithelium include Bmp-4, Sonic hedgehog (Shh), CD44, FGF8, Pitx2 and Otlx-2 genes.

In wild-type embryos, Bmp-4 is initially expressed in the dental epithelium, but expression shifts to the mesenchyme around the tooth buds from E13. 5 (Aberg et al., 1997). At E13. 5 mesenchymal Bmp-4 expression is found only in lower incisors, which are the most advanced developmentally at this stage, whereas expression persists in the epithelium of upper incisors and molars (Ferguson et al., 1998).

Shh is expressed in the epithelial thickening of early tooth germs and is thought to be an important component of the signals that pass from the epithelium to the underlying mesenchyme at this early stage, inducing gene expression in the mesenchyme (Bitgood and McMahon, 1995; Thesleff and Sharpe, 1997). At later stages, Shh is down-regulated but transcripts reappear in the epithelial cells that constitute the enamel knot, a transient signalling centre that arises in the dental epithelium at the late bud stage of tooth development (Ferguson et al., 1998; Vaahtokari et al, 1996).

CD44 and Otlx-2 are expressed more widely in the oral epithelium than Shh (Ferguson et al., 1998; Mucchielli et al, 1997). CD44 encodes the hyaluronan receptor and Otlx-2 is the murine homologue of the human gene which when mutated, causes the disease known as Rieger syndrome in which teeth are absent (Semina et al; 1996).

Follistatin is an activin-binding protein that has been shown to inhibit the activity of activin (Michel et al., 1993; De Winter et al; 1996). The expression pattern of Follistatin may be examined by in situ hybridization analysis (Ferguson et al., 1998).

Follistatin expression is found in tooth germ epithelial cells immediately adjacent to activin expressing cells from E1 1. 5. At later stages, follistatin transcripts are restricted to the columnar-shaped cells that form the outermost layer of the epithelial bud, while the central core of epithelial cells are follistatin-negative (Ferguson et al., 1998). Follistatin is therefore expressed in the tooth epithelium adjacent to and in a complementary pattern to activin in the tooth mesenchyme.

A tooth progenitor cell is one which expresses certain molecular markers characteristic of tooth progenitor cells. For example, a cell would be considered to be a tooth progenitor cell if it expressed one or more tooth mesenchymal cell markers. Examples of such markers include Barx1. Dlx2, Dlx5, Msx1, Pax9, Activin βA, Lhx6, Lhx7 and others. These markers may be detected by any suitable means, such as western blotting, immunofluorescence, radioactive in situ hybridization or other suitable means.

In wild type teeth at the bud stage Barx-1 gene expression is principally found in the molar region of the mandible and maxilla and is present in a broad field of neural crest derived mesenchymal cells rather than being restricted to dental mesenchyme (Ferguson et al., 1998: Tissier-Seta et al., 1995).

Msx-1, Lef-1 and Bmp-4 are expressed in the dental mesenchyme (i.e. the condensing mesenchymal cells associated with invaginating incisor and molar epithelial tooth buds) in response to epithelial signaling (Ferguson et al., 1998; Mackenzie et al., 1991; Kratochwil et al., 1996; Vainio et al., 1993).

Dlx-2 expression is principally found in mesenchymal cells immediately surrounding the epithelial bud, but is also present in the dental epithelium on the buccal side of the buds (Ferguson et al., 1998; Thomas et al., 1995; Qui et al., 1997).

Pax-9, Lhx6 and Lhx7 are expressed in early tooth mesenchyme prior to bud formation and subsequently in condensing mesenchyme at the bud stage (Ferguson et al., 1998; Neubüiser et al., 1997).

Gli-3 is expressed in the mesenchyme from E10. 5. At the bud and cap stage Gli-3 expression is slightly more localized than Par-9 expression, and is concentrated in the dental papilla and dental follicle (Ferguson et al, 1998; Hardcastle and Sharpe, 1998).

Syndecan-1, a cell surface heparin sulphate proteoglycan is transiently expressed in the dental mesenchyme and is thought to regulate dental mesenchymal cell condensation beneath the invaginating dental epithelium (Ferguson et al., 1998; Thesleff et al., 1996).

Tgfβ-1 is found in the dental mesenchyme and weakly in the epithelium of the incisors and only appears in the molars in the dental epithelium at the cap stage (Ferguson et al., 1998; Vaahtokari et al., 1991).

Tgfβ-3 expression is widespread in the mesenchyme of the face, but its expression appears to be substantially absent from the condensing mesenchymal cells immediately adjacent to the epithelial buds of incisors and molars (Ferguson et al., 1998; Chai et al., 1994).

Incubation with the oral epithelial inductive signals is for a time sufficient to produce the tooth progenitor cell. Preferably, this time is at least about 12 hours. Preferably, the time is between 12 and 82 hrs, preferably between 12 and 72 hours. Preferably, the time is between 12 and 24 hours, 12 and 36 hours or 12 and 48 hours.

As discussed in WO 01/60981, the oral epithelial inductive signals may be provided in various ways including: (i) using embryonic oral epithelial cells, (ii) using cells which are not embryonic oral epithelial cells but which express oral epithelial inductive signals and which thereby emulate the signaling characteristics of embryonic oral epithelial cells; and (iii) using purified protein.

In one embodiment of the bone marrow cells are incubated in the presence of one or more embryonic oral epithelial cells to produce the tooth progenitor cell. Preferably, the bone marrow cells are incubated in the presence of embryonic oral epithelium.

As established in WO 01/60981, the role of embryonic oral epithelial cells in providing oral epithelial inductive signals may be replaced by using, inter alia, inductive odontogenic cells which emulate the signaling characteristics of embryonic oral epithelium. WO 01/60981 discloses that odontogenic epithelial cells may be produced from cultured cells which may be engineered to possess characteristics of embryonic oral epithelium, thereby allowing replacement of embryonic oral epithelium with engineered epithelium. Examples of cells which may replace the role of embryonic oral epithelial cells in tooth progenitor production are provided in WO 01/60981 and include immortalized cell lines (e.g. epithelial cells derived from immortalized lines of tooth epithelial cells) and ES cell-derived (i.e. cultured cell derived) epithelial cells.

Accordingly, in an alternative embodiment, the bone marrow cells may be incubated in the presence of one or more inductive odontogenic cells which emulate the signaling characteristics of embryonic oral epithelial cells to produce the tooth progenitor cell.

The inductive odontogenic cells may be produced from non-oral epithelial cells (e.g. epithelial cells derived from immortalized lines of tooth epithelial cells). Preferably, the odontogenic cells are produced from an immortalized cell line or a stem cell (e.g. ES cell).

The inductive odontogenic cells preferably express one, two, three, four or all of the following: FGF8, BMP4, SHH, Pitx2 and Islet1.

As discussed in WO 01/60981, molecular markers may be analyzed to determine whether the signaling properties of early oral epithelium are well established. For instance, expression of FGF8, BMP4, SHH and Pitx2 (the earliest marker of oral epithelium) may be analyzed to determine which cells are likely to be able to replace oral epithelial cells. Methods for testing the odontogenic inducing capacity of cell lines are also disclosed in WO 01/60981.

As discussed in WO 01/60981, if the epithelial cells do not properly induce odontogenesis the expression of inductive signaling molecules (FGF8, BMP4, SHH etc.) may be assayed in collagen explant cultures and any missing signals are replaced either by purified proteins on beads or by electroporation of gene expression constructs.

The combination of secreted signals necessary to induce odontogenesis in bone marrow cells may alternatively be provided using purified protein such as by using the bead delivery system as described in WO 01/60981.

Accordingly, in another embodiment the bone marrow cells may be incubated in the presence of protein-containing beads or protein-coated beads to provide oral epithelial inductive signals to produce the tooth progenitor cell. Persons skilled in the art will readily be able to devise suitable concentrations of the proteins.

Once a tooth progenitor cell has been generated, odontogenic inducing capacity resides in the tooth progenitor cell and naive epithelial cells respond to signals from the tooth progenitor cell and allows tooth primordia and tooth development. If the growth medium used in the cultures does not contain the factors required for the production of an odontogenic epithelium, the culture media may be supplemented with the necessary factors.

The term "tooth primordia" is well known in the art and refers to structures that can develop into fully-formed teeth.

Incubation of the tooth progenitor cell in the presence of one or more epithelial cells is for a time sufficient to produce a tooth primordium. Preferably, this time is at least about 12 hours. Preferably, the tooth progenitor cell is incubated in the presence of oral epithelium.

Preferably, the one or more epithelial cells are oral epithelial cells; embryonic epithelial cells; oral, embryonic epithelial cells; or are epithelial cells derived from stem cells (embryonic stem (ES) cells or adult stem cells) or an immortalized cell line.

Whilst the techniques described in WO2001GB00651 (WO01/60981), PCT/GB2004/000635 (both of which are incorporated herein by reference) and Ohazama et al. (2004) J Dent Res. 2004 July;83(7):518-22 are preferred for the generation of the tooth primordia used in the present invention, the present invention is not restricted to any particular method of generating the tooth primorida. Therefore, methods other than those described in WO2001GB00651 (WO01/60981) and PCT/GB2004/000635 may be used in the present invention.

Tooth Primordia Implantation

The tooth primordia can then be used to generate a tooth in the jaw of the patient by implanting the tooth primordium into a space in the oral cavity and allowing the tooth primordium to develop into a tooth.

Implantation may be achieved by making a small incision in the soft tissues of the maxilla or mandible and placing the explant in the incision and fixing with surgical glue (e.g. Vetbond, 3M).

Tooth and Alveolar Bone Development

Where the tooth is created for the purposes of tooth replacement, it is desirable that the tooth that develops in situ is of the correct shape and size. A number of the genes that determine tooth shape are known, and by manipulation of these genes it is possible to change tooth shape (Tucker et al., 1998; Ferguson et al., 1998; Thomas et al., 1997; Ferguson et al., 2000). Similarly, it is shown experimentally that modulation of signaling event; leads to alteration of tooth size. For example, inhibition of Wnt signaling leads to the development of smaller teeth (Sarkar and Sharpe 2000). These observation could be advantageously employed in the methods of the present invention.

Where jaw augmentation is for the purposes of facilitating denture retention, the tooth primordium once implanted is allowed to develop into a tooth and the tooth is then subsequently removed to leave a bony protruberance which may then be used to grip the patient's denture in place. Where the tooth is to be removed, the management of shape, size, and orientation of the new tooth is obviously not of particular importance.

Sufficient alveolar bone formation will generally occur after about 90 days. Accordingly, it is preferred that the tooth extraction occurs at least 80 or 90 days after implantation of the tooth primordium and more preferably at least after 100, 110, 120, 130, 140, 150, 160 or 170 days after implantation.

Preferably, new tooth formation is stimulated at more than one place in the jaw; preferably new tooth formation is stimulated at least at one place on each side of the jaw. Preferably, tooth formation is stimulated at least two, three, four, five or six sites in the jaw (either in the maxilla (upper jaw) or in the mandible (lower jaw) or both).

New tooth formation may be stimulated in the upper and/or lower jaw depending on the needs of the patient.

Preferably, tooth formation is stimulated in the molar region. Accordingly, in one preferred embodiment tooth formation is stimulated at at least one, two, three, four, five or six sites in the molar region of the jaw.

Where more than one tooth primordium is implanted, the tooth primordia may be implanted at the same time or may be implanted on separate occasions during successive treatments by the medical practitioner overseeing the treatment. In one embodiment, one or more tooth primordia are inserted into one side of the jaw in one treatment and then during a successive treatment one or more tooth primordia are inserted into the other side of the jaw.

Tooth Removal

Where the tooth primordium has been implanted for the purpose of denture retention, the new tooth itself would be superfluous and is removed. Preferably, the new tooth is removed at or around the time of eruption.

Denture Production

Various techniques for denture production are known in the art and will be familiar to the the skilled person. See, for example, 'Textbook of Complete Dentures' by A. O.Rahn, 2002. Pub: B. C.Decker Inc. ISBN 1550091980

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials & Methods

Culture of Non-Dental Cells

Feeder-independent mouse embryonic stem cells (E14.2) were cultured in D-MEM with $10^3$ U/ml of leukaemia inhibitory factor, buffalo rat liver cell-conditional medium, 200 mM L-Glutamine, non-essential amino acid, 2-mercaptoethanol. Medium was changed every day and ES cells were passaged every 2-3 days. Duplicate flasks of the cells were used to generate a mouse gene knock-out that has subsequently resulted in two lines of mice with full germline transmission.

Neural stem cells were isolated from E14 embryo spinal cords at the level of the upper limb to the lower cervical region. The cord itself was carefully dissected free from any other tissue and membrane to reveal nothing but naked spinal cord. The cord was then dissociated into single cells using trypsin and flame-narrow pipettes and plated at 200,000 per T-75 on 10 ∝g/ml poly-omithine and 10 ∝g/ml laminin in serum-free medium (DMEM/F12) containing N2 neural supplement and 20 ng/ml FGF-2. Cells were cultured for 7 days before harvesting (Minger et al., 1996). These tested 99% positive for the neural stem cell marker nestin expression and their ability to differentiate into-different neuronal cell types was assayed in vitro and all three major neuronal cell types, neurons, oligodendrocytes and astrocytes were formed (see supplementary material).

Bone marrow cells were collected from tibiae and femora of 6-9 weeks old female wild-type mice (CD-1). Five mice were killed by cervical dislocation, and tibiae and femurs were aseptically removed and dissected free of adherent tissue. Both ends of the bone were cut, and the bone cavity was flushed out with culture medium slowly injected at the end of the bone using a sterile 21-gauge needle. Bone marrow stromal cells were subsequently suspended in <-minimal essential medium (Sigma) containing 20% heat-inactivated fetal bovine serum (FBS; Gibco BRL) and 100 μM L-ascorbic acid 2-phosphate (Sigma) and were maintained for 10 days in a 75-$cm_2$ tissue flask. The medium was changed after 3 days and then subsequently every 2 days.

C3H10T1/2 and NIH3T3 cells were cultured in Dulbecco's modified Eagle's medium (D-MEM) with 10% FBS. All solutions contained penicillin and streptomycin at 20 IU/ml.

Tissue Recombinations

In order to detect any possible contamination of embryonic oral epithelium with ectomesenchymal cells, we used transgenic mice expressing green fluorescent protein (GFP mice) as the source of the epithelium in the recombinations (Hadjantonakis et al., 1998; Zambrowicz et al., 1997). Following in situ hybridisation, expression of GFP showed that non-dental cells in the recombinations were not contaminated with any ectomesenchyme cells. In situ hybridization for GFP expression on sections of teeth formed in renal capsules showed no expression in any mesenchyme-derived cells whereas sections from teeth produced from GFP mice showed expression in all mesenchyme-derived cells.

Mandible primordia of embryos (E10) from GFP mice were dissected in D-MEM with glutamax-1. The epithelium was isolated following incubation in a solution of Dispase (Gibco BRL) made up in calcium- and magnesium-free PBS at 2 U/ml for 10-15 min at 37° C. After incubation the tissues were washed in D-MEM with 10% FBS, and the epithelium was mechanically separated using fine tungsten needles.

The cultured cell populations consisting of 5-6×$10_6$ cells were harvested by brief exposure to EDTA-Trypsin (2 g/l EDTA and 5 g/l Trypsin). After several washings, the cells were centrifuged to form a pellet which was then placed on transparent Nucleopore membrane filters (0.1 .m pore diameter; Coster) supported by a metal grid following the Trowell technique (1959) as modified by Saxén (1966). Three or four pieces of epithelium were then placed over the cell pellet and the recombinant explants incubated for 1-3 days at 37° C.

After the period of culture, the explants were fixed and processed for in situ hybridization or were transplanted under renal capsules. The explants were cultured in host kidneys for 10 days to allow full development of teeth. The resulting tissues were then fixed and decalcified using 0.5M EDTA (pH 7.6).

In situ Hybridization

For in situ hybridization, explants were embedded and serially sectioned at 7 μm. Sections were split over 5-10 slides. Radioactive in situ hybridization using $^{35}$S-UTP radiolabeled riboprobes was carried out according to previous reports (Angerer and Angerer, 1966; Tucker et al., 1998). The mouse Pax9 cDNA clone was a gift from Rudi Balling.

All experiments involving animals were carried out according to Home Office guidelines covered by Project and Personnel licences to PTS.

Results

Three different sources of non-dental cells were assayed for their odontogenic responses to embryonic oral epithelium in these explant recombinations. Embryonic stem (ES) cells, were used as a pure pluripotent stem cell population that would thus be expected to be able to form dental cells given the appropriate signals. Neural stem cells were used as a pure multipotential stem cell population that is not known to be able to form dental cells. In order to assess the potential of an adult heterogeneous cell population to form teeth, bone marrow-derived (BMD) cells were used. The ES cells were derived from the same passage of cells successfully used to generate germline chimeras. The neural stem cells were derived from a population that tested 99% positive for nestin expression. The BMD cells were a mixed population shown to consist of fibroblasts, osteoblast and adipocyte progenitors and up to 0.01% stem cells (Pereira et al., 1998; Pittenger et al., 1999). Cells were aggregated into a solid mass, overlaid with E10 oral epithelium, cultured in vitro for 3 days and analysed for expression of molecular markers of tooth development. Embryonic stem cells, embryonic neural stem cells and adult BMD cells all responded in an identical way by the induction of Msx1, Lhx7 and Pax9 expression in a total of five recombinations per cell type (FIG. 1, 2A-H). Although each of these genes is expressed in cells other than dental mesenchyme, the combination of expression of these three genes is unique to odontogenic mesenchyme cells (MacKenzie et al., 1992; Grigoriou et al., 1998; Peters et al., 1998). Recombinations were also carried out with cultured non-dental cell populations that are known not to have any multipotential stem cell-like properties, such as NIH3T3 and murine mesenchymal cells (C3H10T1/2) and in these cases no expression of any of the marker genes was observed, while expression of non-odontogenic genes was found (FIG. 2I-L).

Figure 2:
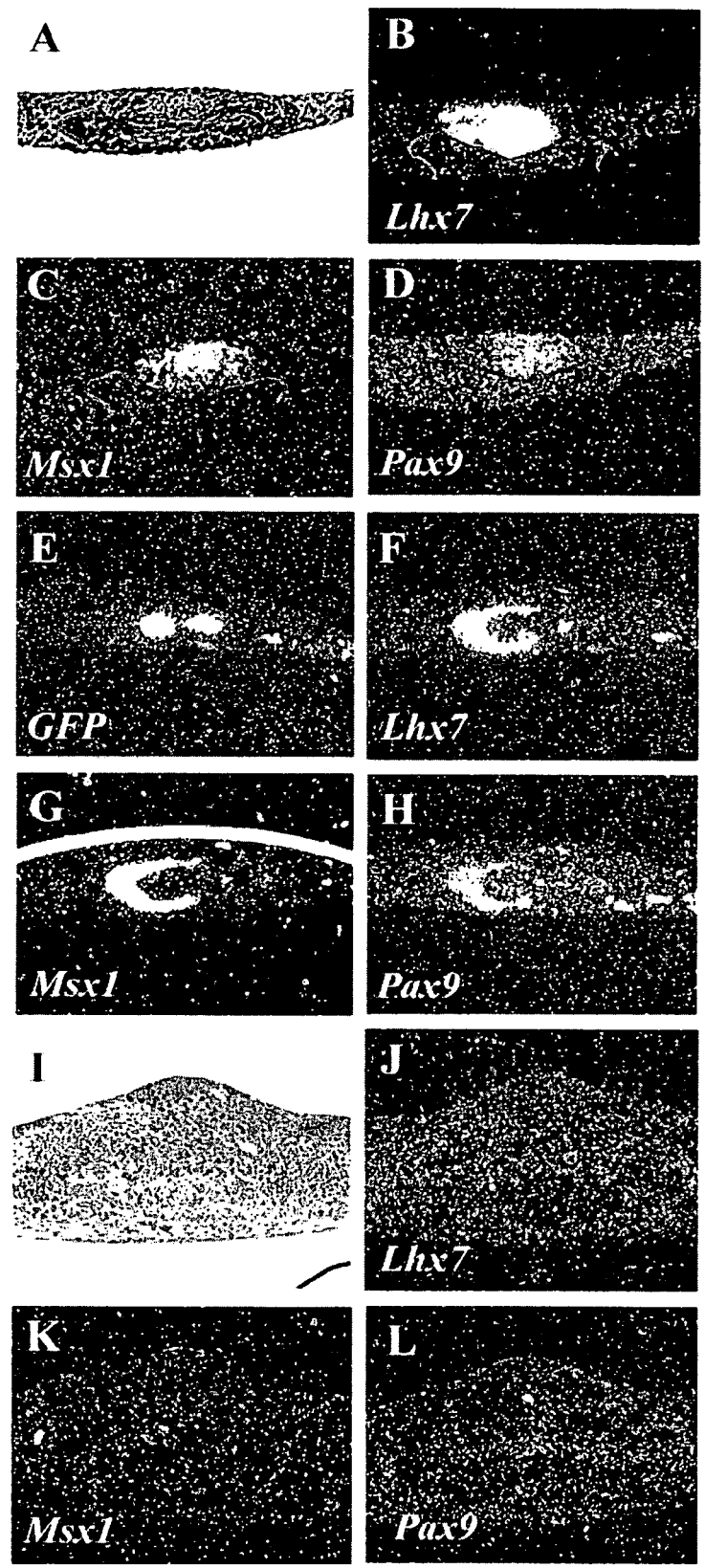
FIGS. 2A-L show sections of heterotypic recombination between neural stem cell aggregations and embryonic oral epithelium (FIGS. 2A-D), between bone marrow-derived cells and embryonic oral epithelium (FIGS. 2E-H) and between NIH3T3 cell aggregations and embryonic oral epithelium (FIGS. 2I-L).

Failure of tooth initiation in these control cultures showed that there was no contamination of the oral epithelium with ectomesenchyme cells. This was also confirmed by using genetically distinct oral epithelium from green fluorescent protein (GFP)-mice, where no expression was detected in non-dental mesenchyme cells in recombinations (FIG. 2E). The odontogenic response of the cultured non-dental "mesenchyme" cell populations thus appears likely to be a stem cell property but one that is not linked to tissue origin or developmental age.

Figure 3:
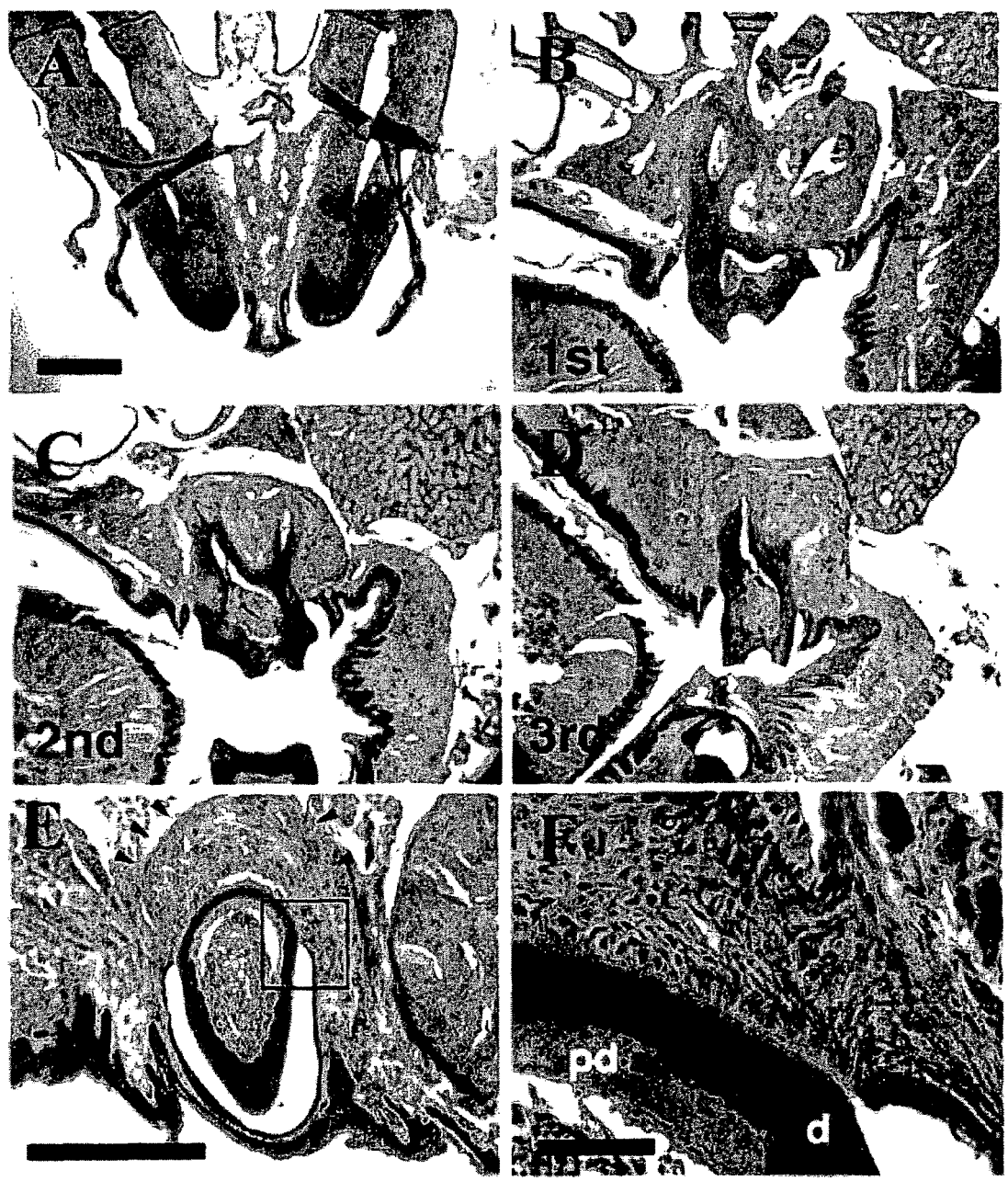
FIGS. 3A-3F show upper jaw teeth in adult mouse mouth 26 days after transplantation of E14.5 molar explants. Molar tooth primordia with surrounding tissue dissected from E14.5 C56/B6 mice were cultured in vitro for 24 hours. The mouse dentition comprises one incisor separated from three molars by a toothless region (diastema) in each quadrant of the mouth. A small incision was made in the soft tissue of the maxilla in the diastema of adult (over 20 weeks) male mice. The explants (approximately 2 mm) were placed in the incision and fixed with surgical glue (Vetbond, 3M). The transplanted explants were left for 26 days with animals being fed a soft diet. After fixation and decalcification, wax serial frontal sections were cut and stained (H&E).
Figure 4:
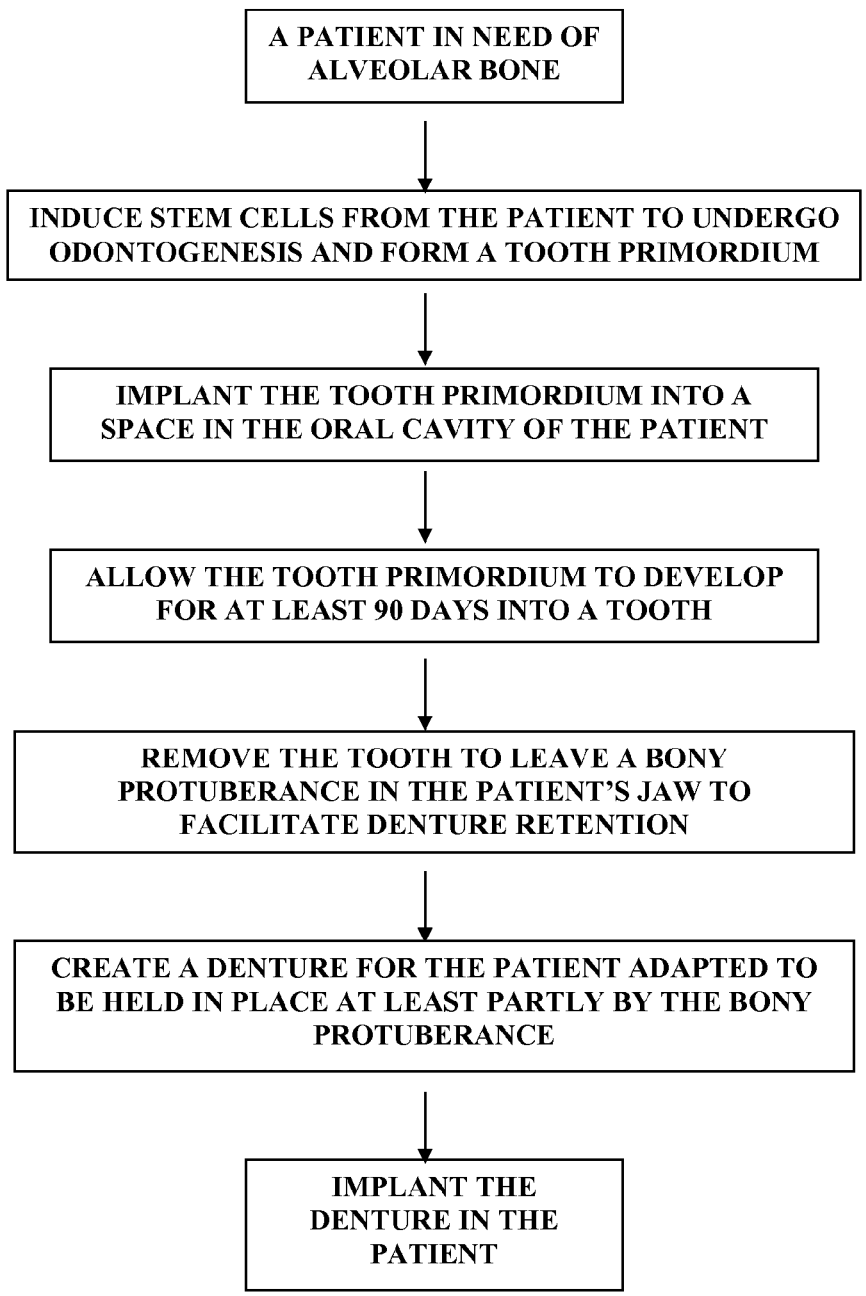
FIG. 4 shows a flow diagram representing and embodiment of the claimed methods.

In order to determine if a mouse embryonic tooth primordium could develop into a tooth when transplanted into the adult mouth, we surgically implanted E14.5 molar tooth rudiments into the soft tissue of the diastema of the maxilla of adult mice. The mouse dentition comprises one incisor separated from three molars by a toothless region (diastema) in each quadrant of the mouth. The transplanted explants were left for 26 days before fixation and decalcification for histology. FIG. 3A-D shows the normal histology of maxillary incisors (A) and molars (B-D). FIG. 3E is a section between incisor (A) and molars (B-D) in the diastema showing a clearly identifiable ectopic tooth formed at the site of the transplantation. The ectopic tooth was of a similar size to the first molar and was histologically normal with dentine and enamel. The tooth was connected to ectopic bone by an organised soft connective tissue (FIG. 3F).

Discussion

The data presented herein show that the odontogenic process can be initiated in non-dental cells of different origins, including purified stem cell populations and a mixed population of adult cells. Bone and soft tissues can be formed from non-dental cell populations consisting entirely of purified stem cells or from a heterogeneous population such as BMD cells. BMD cells have recently been shown to be a convenient, non-pure source of stem cells that can form neurons following bone marrow transplantation in adult mice (Weimann et al., 2003). The ability of this heterogeneous adult cell population to form bone and teeth in tissue engineered rudiments is significant since it implies that a pure population of stem cells is not necessary and this may thus have important implications for the further development of these procedures in humans. The embryonic oral epithelium is a simple, two cell thick ectoderm and it is conceivable that this could be replaced with epithelial cells from another source. If this epithelium can be engineered to express the appropriate signals to initiate odontogenesis, a complete tooth primordium could be produced entirely from cultured cells. The identification of stem cells in dental pulp and from exfoliated deciduous teeth also raises the possibility of using a patient's own tooth cells to generate new tooth primordial (Gronthos et al., 2000; Miura et al., 2003). The ability to tissue engineer an organ rudiment such as a tooth primordium constitutes a major component of a regenerative medicine procedure (Chai and Slavkin 2003). However such organ primordia must be capable of developing into the complete organ in situ, in the appropriate site in the adult body. The renal capsule and anterior chamber of the eye are two adult sites that have been routinely used to support ectopic organ and tissue development because they are immune-compromised and can provide an adequate blood supply to the transplanted tissue. We show here that transfer of embryonic tooth primordia into the adult jaw resulted in complete tooth development, showing that an embryonic primordium can develop in its adult environment and can result in the regeneration of alveolar bone.

REFERENCES CITED

All patents and publications mentioned in the specifications are indicative of the levels of those skilled in the art to which the invention pertains. All patents and publications are herein incorporated by reference to the same extent as if each individual publication was specifically and individually indicated to be incorporated by reference.

Aberg, T., Wozney, J. and Thesleff, I. 1997. Dev. Dyn. 210: 383-396.

Andreasen J O, Paulsen H U, Yu Z, Ahlquist R, Beyer I and Schwartz O. (1990). Eur. J Ortho. 12: 3-13.

Angerer L M, Angerer R C (1992). In situ hybridisation to cellular RNA with radiolabelled RNA probes. In: In Situ Hybridisation: A Practical Approach. Wilkinson D G, editor. Oxford: Oxford University Press, pp. 15-30.

Asashima, M., Nakano, H., Shimada, K., Kinoshita, K., Ishii, K., Shibai, H., and Ueno, N. 1990. Roux'sArch. Dev. Biol. 198: 330-335.

Bagutti C, Wobus A M, Fassler R and Watt F M (1996) Dev. Biol. 179,184-196

Ballas C B, Zielske S P, Gerson S L. J Cell Biochem Suppl 2002;38:20-8

Bianco P and Robey P G (2001). Nature 414, 118-121.

Bianco P, Riminucci M, Gronthos S, Robey P G. Stem Cells 2001;19(3):180-92

Bitgood, M. J. & McMahon, A. P. 1995. Dev. Biol. 172: 126138.

Caplan A I, Bruder S P. Trends Mol Med 2001 June;7(6):259-64

Chai Y and Slavkin H C (2003). Microsc. Res. Tech. 60, 469-479.

Chai, Y., Mah, A., Crohin. C. Groff, S., Bringas, P., Jr., Le, T., Santos, V. and Slavkin, H. C. 1994 Dev. Biol. 162: 85-103.

Chen, Y., Bei, M., Woo, I., Satokata, I. and Maas, R. 1996. Development 122: 3035-3044.

Conlon, F. 1994. Development 120: 1919-1928.

Crossley, P. H. and Martin, G. R. 1995. Development 121, 439-451.

De Winter, J. P., Ten Dijke P., De Vries, C. J. M., Van Acterberg, T. A. E., De Waele, P., Huylebroeck, D., Verschueren, K. and Van den Eijnden-van Raaij, A. J. M. 1996. Mol. Cell Endocrinol. 116: 105-114.

Dohrmann, C. E. Hemmati-Brivanlou, A., Thomsen, G. H. and Fields, A. 1993. Dev. Biol. 157: 474-483.

Dyson, S. and Gurdon, J. B. 1997. Clzrr. Biol. 7: 81-84.

Fainsod, A., Deissler, K., Yelin, R., Marom, K., Epstein. M., Pillemer, G., Steinbeisser, H. and Blum, M. 1997. Alech. Dev. 63: 39-50.

Feijen, A., Goumans, M. J. and van den Eijnden-van Raaij. 1994. Development 120: 3621-3637.

Ferguson C, Tucker A S and Sharpe PT (2000) Development in press.

Ferguson C. A., Tucker A. S., Christiensen L., Lau A. L., Matzuk M. M. and Sharpe P. T. 1998. Genes Dev. 12: 2636-2649

Ferguson C A, Tucker A S, Christensen L, Lau A L, Matsuk M M and Sharpe P T (1998) Genes Dev. 12: 2636-2649

Ferguson C A, Tucker A S, Sharpe P T (2000). Development 127: 403-412.

Gage P J, Suh H and Camper S A (1999) Development 126, 4643-4651

Green, J. B. A., and Smith J. C. 1990. Nature 347: 391-394.

Green, J. B. C., New, H. V., and Smith, J. C. 1992. Cell 71: 731-739.

Grigoriou, M., Tucker, A. S., Sharpe, P. T. and Pachnis, V. 1998. Development, 125:2063-2074

Gronthos S, Mankani M, Brahim J, Robey P G, Shi S (2000). Proc Natl Acad Sci USA 97: 13625-13630.

Hadjantonakis A K, Gertsenstein M, Ikawa M, Okabe M, Nagy A (1998). Mech Dev 76: 79-90.

Hardcastle, Z, Mo, R., Hui, C-c and Sharpe P. T. (1998) Development 125:2803 2811

Heikinheimo, K., Begue-Kim, C., Ritvos, O., Tuuri, T. and Ruch, J. V. 1997. J. Dent. Res. 76: 1625-1636.

Heikinheimo, M., Lawshe, A., Shackleford, G. M., Wilson, D. B. and MacArthur, C. A. Mach. Dev. 48:12-138.

Hemmati-Brivanlou, A., and Melton, D. A. 1992. Nature 359: 609-614.

Hemmati-Brivanlou, A., and Melton, D. A. 1994. Cell 77: 273-281.

Hemmati-Brivanlou, A., Kelly, O. G., and Melton, D. A. 1994. Cell 77: 283-295.

Iseki, S., Araga, A., Ohuchi, H., Nohno, T., Yoshioka, H., Hayashi, F. and Noji, S.1996. Biochem. Biophys. Res. Commun. 218: 688-693.

Ito T, Suzuki A, Okabe M, Imai E, Hori M. Exp Nephrol 2001;9(6):444-50

Kettunen, P. and Thesleff, 1. 1998. Dev. Dyn. 211: 256-268.

Koc O N, Lazarus H M. Bone Marrow Transplant February 2001;27(3):235-9

Kollar, E. J. and Baird G. R. 1969. J Embryol. Exp. Morph. 21: 131-148.

Kratochwil, K., Dull, M., Fari-as, I., Galceran, J. and Grosschedl, R. 1996. Genes Dev. 10: 1382-1394.

Krause D S. Gene Ther 2002 June;9(11):754-8

Lin C R, Kioussi C, O'Connell S, Briata P, Szeto D, Liu F, Izpisua-Belmonte J C and Rosenfeld M G (1999) Nature 401,279-282

Lu M-F, Pressman C. Dyer R, Johnson R and Martin J F (1999) Nature 401,276 278

Lumsden A G. 1988. Development 103:155-169.

MacKenzie A, Ferguson M W, Sharpe P T (1992). Development 115: 403-420.

Mackenzie, A., Leeming, G. L., Jowett. A. K., Ferguson, M. W. J. and Sharpe, P. T. 1991. Development 111: 269-285.

Matzuk, M. M., Kumar, and Bradley, A. 1995b. Nature 374: 356-360.

Matzuk, M. M., Kumar, T. R., Vassalli, A., Bickenbach, J. R., Roop, D. R., Jaenisch, R. and Bradley, A. 1995a. Nature 374: 354-356.

Matzuk, M. M., Lu, N., Vogel, H., Selheyer, K., Roop, D. R., and Bradley, A. 1995c. Nature 374: 360-363.

Michel, U., Famworth, P. and Finlay, J. P. 1993. Mol. Cell Endocrinol. 91: 1-11.

Mina M., and Kollar E. J. 1987. Arch. Oral. Biol. 32: 123-127.

Minger S L, Fisher L J, Ray J, Gage F H (1996). Exp Neurol 141: 12-24.

Minguell J J, Erices A, Conget P. Exp Biol Med (Maywood) 2001 June;226(6):507-20

Miura M, Gronthos S, Zhao M, Lu B, Fisher L W, Robey P G, et al.(2003). *Proc Natl Acad Sci U S A* 100: 5807-5812.

Mucchielli, M., Mitsiadis, T. A., Raffo, S., Brunet, J., Proust, J. and Goridis, C. (1997) Dev. Biol. 189: 275284.

Nakamura. T., Takio, K., Eto, Y., Shibai, H., Titani, K. and Sugino, H. 1990. Science 247: 836-838.

Neubuser, A., Peters, H., Balling, R. and Martin, G. R. 1997. Cell. 90: 247-255.

Ohazama et al. (2004) J Dent Res. 2004 July; 83(7):518-22.

Page, K. M. 1990. Bone. In Theory and Practice of Histological techniques. Third Edition. (ed J. D. Bancroft and A. Stevens), pp. 309-341. Churchill Livingstone, Edinburgh, London, Melbourne and New York.

Pereira R F, O'Hara M D, Laptev A V, Halford K W, Pollard M D, Class R, Simon D, Livezey K, Prockop D J (1998). *Proc Natl Acad Sci USA* 95: 1142-1147.

Peters H, Neubuser A, Kratochwil K, Balling R (1998). *Genes Dev* 12: 2735-2747.

Phinney D G. J Cell Biochem Suppl 2002;38:7-12

Pittenger M F, Mackay A M, Beck S C, Jaiswal R K, Douglas R, Mosca J D, Moorman M A, Simonetti D W, Craig S, Marshak D R (1999). *Science* 284: 143-147.

Pownall, M. E., Tucker, A. S., Slack, J. M. W. and Isaacs, H. V. 1996. Development 122: 3881-3892.

Prockop D J, Azizi S A, Colter D, Digirolamo C, Kopen G, Phinney D G. Biochem Soc Trans 2000;28(4):341-5

Prockop D J. Science 1997 Apr. 4;276(5309):71-4

Qiu, M., Bufone, A., Ghattas, I., Menses, J. J., Sharpe, P. T., Presley, R., Pedersen, R. A.& Rubenstein, J. L. R. 1997. Dev. Biol. 185: 165-184.

Rathjen J, Lake J-A, Bettess M D, Washington J M, Chapmen G and Rathjen P D (1999) J. Cell Sci. 112,601-612 7.

Roberts, V. J. and Barth, S. L. 1994. Endocrinology 128: 914-923.
Roberts, V. J., Sawchenko, P. E. and Vale, W. W. 1991. Endocrinology 128:3122-3129.
Sarkar L and Sharpe P T (2000) J Dent. Res. in press.
Satokata, I. & Maas, R. 1994. Nature Genet. 6: 348-356.
Saxen, L. 1966. J. Exp. Zool. 162: 269-294.
Semina, E. V., Reiter, R., Leysens, N. J., Alward, W. L., Small, K. W., Datson, N. A., Siegel-Bartelt, J., Bierke-Nelson, D., Bitoun, P., Zabel, B. U., Carey, J. C. and Murray, J. C. 1996. Nat. Genet. 14: 392399.
Springer-Verlag, Berlin. van Genderen, C., Okamura, R. M., Fari-as, I., Quo, R. G., Parslow, T. G., Bruhn, L. and Grosschedl, R. 1994. Genes Dev. 8: 2691-9703.
Thesleff, 1. and Sharpe, P. T. 1997. Mech. Dev. 67: 111-123.
Thesleff, I, Vaahtokari, A, & Partanen, A-M. 1995. Int. J. Dev. Biol. 39: 35-50.
Thesleff, I., Vaahtokarin A., Vainio, S. and Jowett, A. 1996. Anatomical Record 245: 151-161.
Thomas B L, Tucker A S, Qiu M, Ferguson C A, Hardcastle Z, Rubenstein J L R and Sharpe P T (1997). Development 124,4811-4818
Thomas, B. T., Porteus, M. H., Rubenstein, J. L. R. and Sharpe, P. T. 1995. Conn. Tiss. Res. 32: 27-34.
Thomsen, G., Woolf, T., Whitman, M., Sokol, S., Vaughan, J., Vale, W., and Melton, D. A. 1990. Cell 63: 485-493.
Tissier-Seta, J. P., Mucchielli, M. L., Mark, M., Mattei, M. G., Goridis, C. and Brunet, J. F. 1995. Mech. Dev. 51: 3-15.
Trowell, O. A. 1959. Exp. Cell Research 16: 118-147.
Tucker A S, Al Khamis A, Sharpe P T (1998). *Dev Dyn* 212: 533-539.
Tucker A S, Matthews K L and Sharpe P T. (1998). Science 282,1136-1138
Vaahtokari, A., Aberg, T., Jermvall, J., Keranen, S. and Thesleff, I. 1996 Azfech. Dev. 54: 39-43.
Vaahtokari, A., Vainio, S. and Thesleff, 1. 1991. Development 113: 985-994.
Vainio, S., Karavanova, I., Jowett, A. and Thesleff, 1. 1993. Cell 75: 45-58.
Vale, W. W., Hseuh, A, Rivier, C. and Yu, J. 1990. In: Peptide growth factors and their receptors II. (ed M. B. Spom and A. B. Roberts), pp. 211-248.
Van Damme A, Vanden Driessche T, Collen D, Chuah M K. Curr Gene Ther 2002 May;2(2): 195-209
Weimann J M, Johansson C B, Trejo A, Blau H M (2003). *Nat Cell Biol* 5: 959-956.
Wilkinson, D. G. 1995. In Situ Hybridisation, A practical approach. IRL Press, Oxford, UK.
Yamashita, H., ten Dijke, P., Huylebroeck, D., Sampath. T. K., Andries, M., Smith, J. C., Heldin, C.-H. and Miyazono, K. 1995. J. Cell. Biol. 130: 217-226.
Young, C. S., Terada, S., Vacanti,J. P., Honda,M., Bartlett,J. D., Yelick,P. C. (2002). *J.Dent.Res.* 81, 695-700.
Zambrowicz B P, Imamoto A, Fiering S, Herzenberg L A, Kerr W G, Soriano P (1997). *Proc Natl Acad Sci USA* 94: 3789-3794.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method for regenerating alveolar bone for facilitating denture retention in a patient in need thereof, the method comprising:
    i) implanting a tooth primordium into a space in the oral cavity of the patient and allowing the tooth primordium to develop into a tooth; and
    ii) removing the tooth to thereby leave a bony protuberance in the patient's jaw to facilitate denture retention.

2. The method according to claim 1 wherein the method further comprises:
    iii) creating a denture for the patient which denture is to be held in place at least partly by the bony protuberance.

3. The method according to claim 1, wherein the tooth primordium is created by inducing stem cells from the patient to undergo odontogenesis.

4. A method of making a denture which is to be retained by the patient at least partly by one or more bony protuberances which have been created by the method according to claim 1, wherein the method of making the denture comprises making a model of at least part of the patient's jaw and using the model to make the denture.

5. The method according to claim 1, wherein the tooth primordium is allowed to develop in the jaw for at least 90 days to thereby form said tooth.

6. The method according to claim 1, wherein a tooth primordium is implanted at least at two places in the jaw to thereby allow the formation of at least two bony protuberances in the jaw of the patient.

7. The method according to claim 6 wherein a tooth primordium is implanted at least at two places in the upper jaw of the patient and at least at two places in the lower jaw of the patient.

* * * * *

UNITED STATES PATENT AND TRADEMARK OFFICE
CERTIFICATE OF CORRECTION

PATENT NO. : 7,497,686 B2
APPLICATION NO. : 11/171965
DATED : March 3, 2009
INVENTOR(S) : Paul T. Sharpe et al.

It is certified that error appears in the above-identified patent and that said Letters Patent is hereby corrected as shown below:

On the Title Page, Item (73) should read:
   Assignees: Odontis Ltd., London (GB); Intercytex Ltd., Manchester (GB)

Signed and Sealed this

Twenty-sixth Day of May, 2009

JOHN DOLL
*Acting Director of the United States Patent and Trademark Office*